United States Patent
Ledingham et al.

(10) Patent No.: US 9,061,166 B2
(45) Date of Patent: Jun. 23, 2015

(54) ANTIPERSPIRANT COMPOSITIONS CONTAINING TRIETHYLHEXANOIN

(75) Inventors: Katherine Ledingham, Farnham Common (GB); Kevin Anthony Ormandy, Leeds (GB)

(73) Assignee: Conopco, Inc., AG West, S. Wing Englewood Cliffs, NJ (US)

(\*) Notice: Subject to any disclaimer, the term of this patent is extended or adjusted under 35 U.S.C. 154(b) by 786 days.

(21) Appl. No.: 13/294,793

(22) Filed: Nov. 11, 2011

(65) Prior Publication Data

US 2012/0121525 A1 May 17, 2012

Related U.S. Application Data

(60) Provisional application No. 61/413,208, filed on Nov. 12, 2010.

(51) Int. Cl.
| | |
|---|---|
| A61Q 15/00 | (2006.01) |
| A61K 8/02 | (2006.01) |
| A61K 8/26 | (2006.01) |
| A61K 8/28 | (2006.01) |
| A61K 8/34 | (2006.01) |
| A61K 8/37 | (2006.01) |
| A61K 8/92 | (2006.01) |

(52) U.S. Cl.
CPC . *A61Q 15/00* (2013.01); *A61K 8/37* (2013.01); *A61K 8/0216* (2013.01); *A61K 8/0229* (2013.01); *A61K 8/26* (2013.01); *A61K 8/28* (2013.01); *A61K 8/342* (2013.01); *A61K 8/375* (2013.01); *A61K 8/92* (2013.01); *A61K 8/922* (2013.01); *A61K 2800/31* (2013.01)

(58) Field of Classification Search
CPC ............ A61K 8/0229; A61K 2800/31; A61K 8/0216; A61K 8/26; A61K 8/28; A61K 8/342; A61K 8/37; A61K 8/92; A61K 8/922; A61Q 5/00

See application file for complete search history.

(56) References Cited

U.S. PATENT DOCUMENTS

| | | |
|---|---|---|
| 6,790,435 B1 | 9/2004 | Ma |
| 6,881,776 B2 | 4/2005 | Butuc |
| 2002/0035046 A1 | 3/2002 | Lukenbach |
| 2002/0058053 A1 | 5/2002 | Nakanishi |
| 2004/0137025 A1 | 7/2004 | Kosugi |
| 2004/0241126 A1 | 12/2004 | Sakuta |
| 2006/0099161 A1 | 5/2006 | Nakane |
| 2008/0311060 A1 | 12/2008 | Sakuta |
| 2009/0074685 A1\* | 3/2009 | Lai .................... 424/59 |
| 2009/0123398 A1 | 5/2009 | Laba et al. |
| 2010/0080832 A1 | 4/2010 | Watanabe |

FOREIGN PATENT DOCUMENTS

| | | |
|---|---|---|
| EP | 2179720 | 4/2010 |
| JP | 48033039 | 7/1973 |
| JP | 2003081802 | 3/2003 |
| JP | 2004051500 | 2/2004 |
| JP | 2008106003 | 5/2008 |
| KR | 2007080644 A \* | 8/2007 |
| WO | WO0006114 | 2/2000 |
| WO | WO0189452 A2 | 11/2001 |
| WO | WO0226198 A1 | 4/2002 |
| WO | WO03000223 A1 | 1/2003 |
| WO | WO2004103308 | 12/2004 |
| WO | WO2005074881 A2 | 8/2005 |
| WO | WO2007119047 A1 | 10/2007 |
| WO | WO2009039158 | 3/2009 |
| WO | WO2008080772 | 6/2009 |
| WO | WO 2010054921 A1 \* | 5/2010 |

OTHER PUBLICATIONS

Ip.com Inc., Schercemo1A AA A Esters, Ip.com Journal, Dec. 17, 2008, Slides 4-6, Slides 24-25, XP013128543, 2008.

\* cited by examiner

*Primary Examiner* — Brian-Yong Kwon
*Assistant Examiner* — Mark V Stevens
(74) *Attorney, Agent, or Firm* — Karen E. Klumas

(57) ABSTRACT

Disclosed are antiperspirant compositions comprising:
a) from 10 to 35 wt. %, based on the total weight of the composition, of antiperspirant active;
b) triethyl hexanoin,
c) at least one additional non-volatile oil, and
d) from 1.5 to 30 wt. %, based on the total weight of composition, of structurant,
wherein:
the ratio, by weight, of triethylhexanoin to additional non-volatile oil is from 5:1 to 1:2;
in combination, triethylhexanoin and additional non-volatile oil provide from 35 to 65% of the total weight of the composition;
the composition contains from 0 to 5 wt. % of volatile silicone oil;
the composition is anhydrous; and
the composition is in the form of a solid or soft solid.
Also disclosed are methods of making such stick compositions, and methods of ameliorating perspiration by the topical application of such compositions to the skin.

15 Claims, No Drawings

ANTIPERSPIRANT COMPOSITIONS CONTAINING TRIETHYLHEXANOIN

This application claims priority to provisional application Ser. No. 61/413,208, filed Nov. 12, 2010.

BACKGROUND OF THE INVENTION

Solids and soft solids are widely used forms of antiperspirant products. Such products commonly comprise antiperspirant active, carrier oil and structurant. The majority of these solid and soft solid products are anhydrous suspensions, a large portion of which employ fatty alcohol, e.g., stearyl alcohol, optionally in combination with one or more additional structurants. In such products, the antiperspirant active commonly comprises astringent aluminum salt, typically astringent aluminum/zirconium salt, suspended in a matrix formed by a combination of carrier oil and structurant.

The literature suggests numerous volatile and non-volatile oils for use in antiperspirant suspension compositions. To impart desirable sensory properties a large portion, frequently upwards of 40% of the carrier oil, is comprised of volatile oil. Volatile oil tends to impart a clean, dry feel to the applied composition, as well as to contribute to smooth product application and glide. Additionally, volatile oil aids in fragrance delivery.

Within the industry, the volatile oil of choice is commonly volatile silicone oil, e.g., cyclomethicone. Cyclomethicone is nominally designated as D4, D5 or D6, depending upon the particular cyclomethicone (e.g., cyclotetrasiloxane, cyclopentasiloxane or cyclohexasiloxane) predominant therein. The widespread use of cyclomethicone in anhydrous antiperspirant suspensions stems, in part, from its solubility and/or compatibility with numerous carrier oils and structurant ingredients, as well as on the ability of the material to contribute a clean, dry, silky feel to the compositions in which it is employed. While cyclomethicone has sufficient volatility to impart desirable sensory attributes, compared to many other volatile oils, a significant amount of the cyclomethicone tends to be retained in the suspension composition, as opposed to being lost to evaporation. Volatile retention plays an important role in a product delivering equivalent sensory performance over its useful pack life and is also a factor in product stability. Additionally, the surface tension and spreadability of cyclomethicone contributes to products having a smooth or silky feel on application.

When the processing temperature required by the structurant exceeds the flash point of one or more oil components (which is frequently the case when volatile oil is present) processing and material handling considerations may complicate production. Minimizing volatile oil may offer producers certain manufacturing advantages, and may also be desirable from an environmental or regulatory perspective.

In addition to antiperspirant suspension compositions, cyclomethicone is the volatile oil of choice in many other cosmetic products, including products for skin and hair. Cyclomethicone generally, and D5 in particular, is much in demand across a large segment of the cosmetics industry. Recently, the widespread use of cyclomethicone has given rise to issues regarding material availability and sourcing.

While reducing volatile oil content may be desirable conceptually, the concept represents presents considerable formulation difficulties given both the relatively high level at which volatile oil is typically present in antiperspirant suspension compositions and the functions that it performs (which functions are, to a large extent, linked to the material's volatility). Significantly reducing the volatile content of such antiperspirant compositions represents a fundamental change to industry practice. Not only must the replacement material meet the health and environmental requirements for cosmetic products, it should also satisfy the processing requirements of the products into which it is incorporated. Additionally, the replacement material should not degrade a product's physical properties to an unacceptable extent. Desirably, the replacement material should provide a composition that, in use, delivers acceptable sensory and aesthetic properties (e.g., low whiteness, smooth texture and acceptable fragrance to name a few).

Removing volatile oil can result in antiperspirant compositions that are perceived as being greasy, oily, and/or sticky, and/or as taking a relatively long time to dry. Additionally, reformulation to remove volatile oil can significantly affect the physical properties of the composition itself, e.g. payout, hardness, integrity, uniformity, and the like, as well as the texture, whiteness, and appearance of the deposited product. The materials that replace the volatile oil can also give rise to different sensory characteristics depending not only on the properties of the replacement materials themselves, but also on the particular base compositions into which the replacement materials are incorporated. That is to say, performance of a replacement material can be impacted by structurant and oils with which the replacement material is employed.

Reformulation is also impacted by the relatively high level of antiperspirant active present in antiperspirant compositions, typically 10 weight percent or more. Moreover, the antiperspirant active particles are generally of such a size and weight that relatively rapid cooling is required to limit settlement thereof during cooling. Particle sedimentation can give rise to a non-uniform distribution of active in the solidified product; in turn, this can give rise to differences in the delivery of active over the useful pack life. Sedimentation can be exacerbated when the difference between the melt or processing temperature and the solidification temperature is relatively high.

To inhibit sedimentation, antiperspirant suspension compositions, and suspension sticks in particular, tend to be cooled relatively rapidly. By way of comparison, cosmetic suspensions that lack a suspended solid prone to settlement, e.g., lipsticks, may be cooled more slowly. Rapid cooling, while useful in limiting settlement, can give rise to issues with respect to solidification/crystallization of the structurant and the quality of the resulting product. Removing a substantial portion of volatile oil in an antiperspirant suspension composition can impact solidification, crystallization and/or sedimentation behavior.

The presence of antiperspirant active can pose addition complications from a sensory perspective. Even in compositions having volatile oil to contribute to desirable sensory properties, the size and relatively high content of suspended antiperspirant particles may present challenges as regards overcoming active associated drag, particularly in solid sticks. Overcoming drag can be more difficult when the volatile oil content of a composition is reduced.

There remains a need for an antiperspirant composition in the form of a solid or soft solid suspension composition that provides desirable sensory properties when applied to the underarm, in which composition volatile silicone oil and, more desirably volatile oil (exclusive of perfume oil) in general, is reduced or eliminated.

Accordingly, it is an object of the present invention to provide an antiperspirant composition that overcomes or ameliorate one or more of the issues disclosed above.

SUMMARY OF THE INVENTION

It has been found that through the use of particular combinations of triethylhexanoin, additional non-volatile emollient oil, and structurant, it is possible to reduce or eliminate volatile silicone oil and, in one or more embodiments volatile oil (exclusive of perfume oil), while providing anhydrous solid or soft solid antiperspirant compositions that afford desirable sensory properties when applied to the underarm.

In one embodiment of this invention there is provided an antiperspirant composition comprising;
  a) from 10 to 35 wt. %, based on the total weight of the composition, of antiperspirant active;
  b) triethylhexanoin,
  c) at least one additional non-volatile oil, and
  d) from 1.5 to 30 wt. %, based on the total weight of the composition, of structurant,
wherein:
  the ratio, by weight, of triethylhexanoin to additional non-volatile oil is from 5:1 to 1:2;
  in combination, triethylhexanoin and additional non-volatile oil provide from 35 to 65% of the total weight of the composition;
  the composition contains from 0 to 5 wt. % of volatile silicone oil;
  the composition is anhydrous; and
  the composition is in the form of a solid or soft-solid.

In another embodiment, there is provided a method of ameliorating perspiration by the topical application to the skin of an antiperspirant active, by means of an antiperspirant composition according to this invention.

In yet another embodiment, there is provided a method of producing an anhydrous solid or soft solid antiperspirant composition according to this invention, which method comprises the steps of:
  a) forming at an elevated temperature, a fluid mixture comprising the antiperspirant active suspended in the oil in which the structurant is dispersed and/or dissolved; and
  b) cooling or permitting the fluid mixture to cool to a temperature at which the fluid mixture sets.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about". All amounts are by weight of the final composition, unless otherwise specified.

The antiperspirant compositions contemplated herein are suspension compositions that at 25° C are in the form of solids or soft solids. The solid compositions are further characterized as retaining their shape without lateral support under the influence of the Earth's gravity, at temperatures up to at least 50° C.

The antiperspirant composition of this invention is an anhydrous composition. As used herein "anhydrous" means that the composition either contains no free water or, that if free water is present, the amount thereof is not more than 1 wt. %, based on the total weight of the antiperspirant composition. In the practice of this invention it is particularly desirable that, if free water is present, the amount thereof is less than 0.5% of the total weight of the antiperspirant composition. Bound or complexed water, as, for example, water of hydration in the antiperspirant salt, is deemed not to be "free". In one embodiment, the composition is free or substantially free of lower $C_1$ to $C_6$ mono- and dihydric alcohols such as, for example, ethanol, propanol, butane diol, and the like. In the context of such lower alcohols "substantially free" means that, if present, the total amount thereof does not exceed 5 wt. % of the antiperspirant composition. In one or more embodiments it is preferred that the total amount of such alcohols does not exceed 3 wt. % of the antiperspirant composition and, more particularly, does not exceed 1 wt. % of the antiperspirant composition. In one or more embodiments the antiperspirant composition is formulated as a suspension composition in which antiperspirant active is dispersed in a single-phase hydrophobic carrier; that is to say, the composition is not an emulsion.

Antiperspirant Active

The antiperspirant actives used herein are often selected from astringent active salts including, in particular, one or more aluminum, zirconium and mixed aluminum/zirconium salts, optionally complexed. Preferred aluminum, zirconium and aluminum/zirconium salts contain a halide, especially chloride and especially preferred salts are basic salts, which is to say a fraction of the halide within the empirical formula has been replaced by bound hydroxyl groups. Halohydroates, particularly chlorohydrate salts are very highly desired.

Aluminium halohydrates are usually defined by the general formula $Al_2(OH)_xQ_y\cdot wH_2O$ in which Q represents chlorine, bromine or iodine, x is a variable from 2 to 5 and x + y=6, and $wH_2O$ represents a variable amount of hydration. Aluminium chlorohydrate as made comprises a mixture of a number of different polymeric species in varying proportions, depending on the molar ratio of aluminium to chloride and the conditions employed during manufacture. All such mixtures are employable herein. In one or more embodiments it is of interest to employ what is commonly called activated aluminium chlorohydrate or enhanced activity aluminium chlorohydrate, sometimes abbreviated to AACH, in which the proportion of the more active species is higher by virtue of its method of manufacture. AACH is often made by recovery of an aluminium chlorohydrate from a dilute solution under strictly controlled reaction/maturing/dewatering/drying conditions. AACH is commercially available by name, or as activated or enhanced activity material, from suppliers such as Reheis, Summit Research and B K Giulini.

Zirconium actives can usually be represented by the empirical general formula: $ZrO(OH)_{2n-nz}B_z\cdot wH_2O$ in which z is a variable in the range of from 0.9 to 2.0 so that the value 2n-nz is zero or positive, n is the valency of B, and B is selected from the group consisting of chloride, other halide, sulfamate, sulfate and mixtures thereof. Possible hydration to a variable extent is represented by $wH_2O$. Preferably B represents chloride and the variable z lies in the range from 1.5 to 1.87. In practice, such zirconium salts are usually not employed by themselves, but as a component of a combined aluminum and zirconium-based antiperspirant.

The above aluminum and zirconium salts may have coordinated and/or bound water in various quantities and/or may be present as polymeric species, mixtures or complexes. In particular, zirconium hydroxy salts often represent a range of salts having various amounts of the hydroxyl group. Aluminum zirconium chlorohydrate may be particularly preferred.

Antiperspirant complexes based on the above-mentioned astringent aluminum and/or zirconium salts can be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine which has the formula $CH_2(NH_2)COOH$.

It is preferred in some embodiments of the instant invention to employ complexes of a combination of aluminum halohydrates (especially chlorohydrates) and zirconium chlorohydrates together with amino acids such as glycine, which are disclosed in U.S. Pat. No. 3,792,068 (Luedders et al). Certain of those Al/Zr complexes are commonly called ZAG in the literature. ZAG actives generally contain aluminum, zirconium and chloride with an Al/Zr ratio in a range from 2 to 10, especially 2 to 6, an Al/Cl ratio from 2.1 to 0.9 and a variable amount of glycine. Actives of this preferred type are available from manufacturers that include SummitReheis. In one preferred embodiment, the antiperspirant salt is an activated aluminum zirconium tetrachlorohydrate complex with glycine, herein referred to as AAZG.

Other antiperspirant actives which may be utilized include astringent titanium salts, for example those described in GB 2299506A.

The amount of antiperspirant active present in the compositions of this invention is from 10 to 35 wt. %, with compositions comprising from 15 to 30 wt. % of antiperspirant active being of particular interest. In at least one embodiment of this invention, the antiperspirant composition comprises from 18 to 25 wt. % of antiperspirant active.

The mean particle size of the antiperspirant active in the antiperspirant feedstock is commonly in the range of 0.1 to 100 µm, with feedstocks in which 95% by weight of the antiperspirant active particles have a particle size below 50 microns, being of particular interest. In one embodiment of interest, the antiperspirant active, as added, has a mean particle size of from 3 to 30 µm, more particularly from 5 to 25 µm. In one preferred embodiment, the antiperspirant active, as added, has a mean particle size of from 10 to 25 µm.

Triethylhexanoin and Additional Non-Volatile Oil

As used herein the term "volatile" is used to designate a material having a vapor pressure at 25° C. that is at least 1 Pa. (and for many volatile materials is up to 2 kPa or higher at 25° C.). A non-volatile material can be considered to generate a vapour pressure of below 1 Pa at 25° C. (and for many non-volatile materials is less than 0.1 Pa). As used herein, the term "oil" refers to a water immiscible (alternatively described as hydrophobic or lipophilic) material that is liquid at a temperature of 20° C. Preferably the oil is further characterized as having a boiling point above 100° C., more preferably above 150° C.

The subject antiperspirant composition includes triethylhexanoin, itself a non-volatile oil, and at least one additional non-volatile oil. Triethylhexanoin is commercially available; for example, Croda offers the material under the trade name Crodamol™ GTEH and Uniqema offers the material under the trade name Estol™ 3609.

In one embodiment of interest, the triethylhexanoin is present in an amount of from 15 to 40 wt %, preferably from 20 to 35 wt %, based on the total weight of the antiperspirant composition.

Classes of oils from which the at least one additional non-volatile oil may be selected include silicone oils, hydrocarbon oils, alcohol oils, ester oils, and ether oils. The non-volatile oils may be present as mixtures of two or more oils taken from one or more of these oil classes.

Non-volatile silicones suitable for use herein include, for example, polyalkylsiloxane, polyalkarylsiloxane and polyethersiloxane copolymers. These can suitably be selected from dimethicone and dimethicone copolyols. Commercially available non-volatile silicone oils are available from various suppliers including for, example, Dow Corning. When present, the non-volatile silicone oil often desirably comprises up to 5 wt. % of the antiperspirant composition. In at least one embodiment of this invention, the non-volatile silicone oil is present in the antiperspirant composition in an amount of from 0.5 to 3 wt. %. In another embodiment of interest the subject composition contains less than 1% of silicone wax; in yet another embodiment, the composition is free of non-volatile silicone oil and/or silicone wax.

Hydrocarbon oils suitable for use herein may be saturated or unsaturated. The non-volatile hydrocarbon oils often contain from 12 to 40, more particularly, from 20 to 40 carbons on average and include mineral oils, hydrogenated polydecene, hydrogenated polyisobutene and the like.

Non-volatile alcohol oils include, for example, branched chain monohydric alcohols containing from 12 to 40 carbon atoms, and often from 14 to 30 carbon atoms such as, for example, isostearyl alcohol.

Among the suitable ester oils are aliphatic esters, aromatic esters (which term as used in the instant specification and claims includes mixed aromatic/aliphatic ester oils), and triglyceride oils. Suitable aliphatic esters are esters that contain at least one long chain alkyl group such as esters derived from $C_1$ to $C_{20}$ alkanols esterified with a $C_6$ to $C_{22}$ alkanoic acid or $C_6$ to $C_{10}$ alkanedioic acid. Among the suitable aromatic esters are $C_8$-$C_{18}$ alkyl benzoates or mixtures thereof including, in particular, $C_{12}$-$C_{15}$ alkyl benzoates. Many suitable aromatic esters are available under the trademark Finsolv. Other aromatic esters which can be contemplated for use herein comprise double aromatic inclusion. Preferred double aromatic esters comprise a linear or branched alkyl chain, e.g. from 1 to 3 carbons, interposed between ester and/or ether substituted phenyl groups.

Among the triglyceride oils suitable for use herein are natural oils derived from plants. The natural oils desirably comprise one or more triglycerides of oleic acid, linoleic acid, linolenic acid or ricinoleic acid. Various isomers of such acids often have common names, including linolenelaidic acid, trans 7-octadecenoic acid, parinaric acid, pinolenic acid punicic acid, petroselenic acid and stearidonic acid. It is especially desirable to employ glycerides derived from oleic acid, linoleic acid or petroselenic acid, or a mixture containing one or more of them.

Natural oils containing one or more of such triglycerides include, for example, coriander seed oil for derivatives of petroselinic acid, impatiens balsimina seed oil, parinarium laurinarium kernel fat or sabastiana brasilinensis seed oil for derivatives of cis-parinaric acid, dehydrated castor seed oil, for derivatives of conjugated linoleic acids, borage seed oil and evening primrose oil for derivatives of linoleic and linolenic acids, aquilegia vulgaris oil for columbinic acid and sunflower oil, olive oil or safflower oil for derivatives of oleic acid, often together with linoleic acids. Other suitable oils are obtainable from hemp, which can be processed to derive stearadonic acid derivatives and maize corn oil. A natural oil that by virtue of its characteristics and availability is of particular interest comprises sunflower oil.

In one or more embodiments, the amount of natural oil is 0 to 3 wt. %, more particularly from 0.1 to 3 wt. %, and even more particularly, from 0.5 to 2 wt. %, based on the total weight of the composition. Higher levels of natural oil may, however, be desirable in some embodiments.

Ether oils suitable for use herein comprise liquid aliphatic ethers, including, for example alkyl ethers of polypropylene glycol (PPG), the alkyl group comprising from 2 to 6, and especially 4 carbon atoms and the PPG moiety comprising from 10 to 20 and particularly 14 to 18 propylene glycol units. One preferred ether oil bears the INCI name PPG14-butyl ether.

In one embodiment of interest the additional non-volatile oil comprises an aliphatic polyether and, optionally, an aromatic ester oil. When both aliphatic ether oil and aromatic ester oil are present, in one or more embodiments the weight ratio of ester oil to ether oil is from 3:1 to 1:3, preferably from 2:1 to 1:2. In one embodiment, a weight ratio of 1.5:1 to 1:1.5 is of particular interest.

The additional non-volatile oil should not detract from the sensory and aesthetic properties desired. As demonstrated in the Examples that follow, some non-volatile oils can be malodorous. Where odour is an issue, the oils should be eliminated or kept to such a low level that they do not negatively impact fragrance.

In combination, triethylhexanoin and additional non-volatile oil provide from 35 to 65%, more particularly from 40 to 60%, even more particularly, from 45 to 60% or from 50 to 60% of the total weight of the composition. The ratio, by weight, of triethylhexanoin to additional non-volatile oil is from 5:1 to 1:2, with ratios of 2.5:1 to 1:1.5 and, more particularly, from 2:1 to 1:1 being of interest in one or more embodiments. In other embodiments, ratios of from 1.75:1 to 1.25:1 are of interest.

The subject composition may also comprise a minor amount of volatile oil. The amount of volatile silicone oil, if present, should not exceed 5 wt. % of the antiperspirant composition. Preferably, the amount of volatile silicone, if present, does not exceed 3 wt. % of the antiperspirant composition and more preferably does not exceed 1 wt. % of the antiperspirant composition. Of particular interest in one or more embodiments are antiperspirant compositions that are free of volatile silicone oil. Preferably the antiperspirant composition contains from 0 to 5 wt. % of volatile oil (exclusive of perfume oil), with compositions that contain from 0 to 3 wt. %, more particularly from 0 to 1 wt. %, of volatile oil (exclusive of perfume oil) being of particular interest. In one or more embodiments the antiperspirant compositions are free of all volatile oil (exclusive of perfume oil).

Perfume oil may include volatile and non-volatile oil and may be present as free and/or encapsulated fragrance. For purposes of this invention, unless otherwise indicated, perfume oil is considered as a separate component, and the amount thereof is not included as part of either the "additional non-volatile on" or the minor amount of "volatile on" otherwise permitted in the subject compositions. The total amount of perfume oil (inclusive of all material present as part of fragrance encapsulate) is often from 0.001 to 5 wt. %, more particularly from 0.01 to 4 wt. %, and, even more particularly, from 0.1 to 3 wt %, based on the total weight of the composition. Encapsulated fragrance may be formulated as shear or moisture sensitive materials.

Structurant

In the practice of this invention, the structurant functions to gel or solidify the carrier oil. Commonly, the gelation arises by forming a mobile liquid oil phase at an elevated temperature throughout which the structurant is distributed, and in particular by dissolution, such that when the composition cools or is cooled below its setting temperature, a solid product is obtained.

The structurant used herein usually selected from waxes, polymeric gellants and non-polymeric fiber-forming gellants, such waxes and gellants optionally being supplemented by particulate thickener. Structurant is generally employed at a level of from 1.5 to 30 wt. %, more particularly from 3 to 30 wt. %, and, in some embodiments, from 6 to 28 wt %, more particularly from 10 to 25 wt %, with the range of preference being determined by the choice of structurant and the particular form of the composition (i.e., a solid or soft solid) desired. For example, in the context of wax sticks, in some embodiments a minimum amount of 6 wt. % or, in some instances, a minimum amount of 10 wt. % of structurant may be desired.

The term "wax" refers to materials that are solid at 30° C.; melt to give a mobile liquid at temperature above 40° C. and generally below 95° C.; are water-insoluble and remain water-immiscible when heated above their melting point. Examples of waxes suitable for use herein include ester waxes, fatty alcohols, hydrocarbon waxes, and polyethylene waxes. The waxes may be synthetic or naturally occurring or derived by processing of naturally occurring products, such as by hydrogenating unsaturated oils. Naturally occurring waxes or waxes derived from naturally occurring oils are often mixtures of compounds which include a substantial proportion, likely to be a majority, of fatty esters.

Examples of ester waxes include esters in the range of $C_{16}$ to $C_{40}$ fatty acids with glycerol or ethylene glycol and these may be made synthetically. The esters include, for example, glyceryl di- or tri-esters and glycol diesters. Commonly, the ester component of glycol or glyceryl waxes are derived from selected narrower ranges of fatty acids, such as from $C_{16}$ to $C_{22}$ or $C_{24}$, predominately $C_{18}$ or $C_{20}$ to $C_{36}$ or $C_{40}$ acids. Alternately, the product can comprise glyceryl or glycol esters derived from natural products, such as hydrogenated castor oil often referred to as castor wax. The ester waxes or significant individual components of ester wax mixture include glyceryl palmitate, glyceryl stearate, glyceryl behenate, glycol stearate and glycol behnate. A number of suitable ester waxes are sold by Croda under the trade mark Syncrowax or by Koster Keunen under the trade mark Kesterwax.

Examples of natural waxes include beeswax, spermaceti, bayberry, carnauba and candelilla waxes that are of vegetable origin and mineral waxes from fossil remains other than petroleum.

Suitable fatty alcohols for use herein include $C_{16}$ to $C_{24}$, more particularly, $C_{18}$ to $C_{22}$, linear fatty alcohols such as, for example, stearyl alcohol, cetyl alcohol and behenyl alcohol. Among the fatty alcohols, stearyl alcohol is of particular interest. In one embodiment of this invention $C_{18}$—$C_{22}$ fatty alcohols comprise from 90 to 100% by weight, preferably from 95 to 100% by weight of the total fatty alcohol present in the subject compositions. Hydrocarbon waxes suitable for use herein include paraffin wax, Fiscer-Tropsch waxes, and microcrystalline wax.

When employing wax structurant, it is often preferable to employ a combination of waxes, differing for example by their chemical constitution and/or their melting point.

In one embodiment of particular interest, the subject antiperspirant composition contains from 15 to 28 wt. % of wax structurant, based on the total weight of the composition and is further characterized as containing fatty alcohol in an amount of from 12 to 24% wt. %, especially from 15% to 22 wt. %, based on the total weight of the composition. Other embodiments contemplate the use of lesser amounts of fatty alcohol, with yet other embodiments being compositions that are free of fatty alcohol.

When fatty alcohol or lower melting point hydrocarbon structurant is present, it is often of interest to employ one or more co-structurants having a melting point of 75 to 95° C., and especially from 80-90° C. Ester waxes and/or polyethylene are of particular interest as co-structurant. The co-structurant is often present in the antiperspirant composition in an amount of from 2 to 12 wt %, especially from 2 to 8 wt. %, based on the total weight of the composition, with ranges of from 3 to 6 wt. % based on the total weight of the composition often being of interest. Castor wax and polyethylene wax, especially polyethylene having a weight average molecular weight of from 200 to 2000, more particularly, from 200 to 1000, and even more particularly from 300 to 600, are among the co-structurants that are especially well-suited for use in the subject compositions.

Non-polymeric fiber-forming gellants suitable for use herein dissolve in a water-immiscible blend of materials at elevated temperature and on cooling precipitate out to form a network of very thin strands that are typically no more than a few molecules wide. One particularly effective category of such structurants comprises N-acyl amino acid amides, in particular N-acyl glutamic acid dialkyhlamides, such as N-lauroyl glutamic acid di-n-butylamide and N-ethylhexanoyl glutamic acid di-n-butylamide and especially mixtures thereof. Other classes of non-polymeric fiber-forming structurants, that may be employed in the subject compositions includes, for example, 12-hydroxystearic acid and cyclodipeptides as describe, for example, in U.S. Pat. No. 7,332,153. When present, the non-polymeric fiber-forming gellants are often employed in amounts of from 1.5 to 16%, and especially from 3 to 12%, based on the total weight of the composition. Notwithstanding the foregoing, in one or more embodiments of interest the composition is free of amide gellants.

Included among the polymeric gellants suitable for use herein are siloxan-based polyamides such as described for example, WO 99106473 incorporated herein by reference.

Particulate thickening agents include, for example, particulate silica (fumed silica being of particular interest in one or more embodiments) or clay (for example bentonite and/or hectorite). Fumed silica is commercially available from Degussa under the trademark Aerosil and clays are available from Rheos under the trademark Bentone. Thickening particles are described in U.S. Pat. No. 6,387,358. Inorganic particulates, including for example, talc and fumed silica, when present, typically do not exceed 5 wt. % of the composition and often do not exceed 3 wt. % of the antiperspirant composition, although particulate filler levels up to 10% may be used in some compositions. In one embodiment the compositions are obtained without incorporation of particulate thickening agents.

The amount and selection of structurant depends, in pa on the type and hardness of the composition desired.

In one or more embodiments, the subject in antiperspirant compositions are free of non-polymeric fiber-forming gellants and/or polymeric gellants. In one or more embodiments, the compositions of interest are free of cholyesteryl derivatives.

Soft solids are generally characterized as having a hardness of from 0.003 to 0.5 Newton/mm$^2$, and commonly from 0.003 or 0.01 up to 0.1 Newton/mm$^2$. Hardness can be measured using a Stable Micro systems TA.XT2i Texture Analyser. A metal sphere, of diameter 9.5 mm, is attached to the underside of its 5 kg bad cell, and positioned just above the sample surface. Under control of Expert Exceed™ software, the sphere is indented into the sample at an indentation speed of 0.05 mm/s for a distance of 7 mm and reversed to withdraw the sphere from the sample at the same speed. Data comprising time(s) distance (mm) and force (N) is acquired at a rate of 25 Hz. The hardness H at a penetration of 4.76 mm is calculated using the formula:

$$H=F/A$$

In which H expressed in N·mm$^{-2}$, F is the bad at the same traveled distance in N and A is the projected area of the indentation in mm$^{-2}$.

Solid sticks herein commonly have a hardness as measured in a conventional penetration test of 4-16 mm, preferably from 6-14 mm. Many have a penetration of from 7-13 mm or, more particularly, from 7-10 mm. The conventional penetration test employed herein utilizes a PNT penetrometer equipped with a Seta wax needle (weight 2.5 grams) which has a cone angle at the point of the needle specified to be 9°10'±15', A sample of the composition with a flat upper surface is used. The needle is lowered onto the surface of the composition and then a penetration hardness measurement is conducted by allowing the needle with its holder to drop under the combined weight of needle and holder of 50 grams for a period of five seconds after which the depth of penetration is noted. Desirably the test is carried out at six points on each sample and the results are averaged to provide what is herein referred to as a "Penetration Value".

In a preferred embodiment the antiperspirant compositions of this invention further comprise one or more additional optional components selected from the group consisting of: wash-off agents; skin feel improvers; skin benefit agents; colorants; preservatives; humectants; and emulsifiers. These additional optional components combined often do not exceed 10 wt. % of the antiperspirant composition and often do not exceed 5 wt. % of the composition. Among the wash-off agents suitable for use herein are non-ionic surfactant, often having an HLB value of from 6 to 15, especially polyalkylene oxide (e.g. PEO or PEO/PPO), and ether or ester derivatives of fatty alcohol or fatty acid, such as, for example, seteth-15, steareth-25 and ceteareth-20. Some of the additional optional ingredients, for example preservative, are often present in relatively small amounts, for example, less than 1 wt. % or even less than 0.5 wt % or less than 0.25 wt % of the composition.

In an embodiment of particular interest the subject antiperspirant composition comprises
  a) from 10 to 35 wt. %, based on the total weight of the composition, of antiperspirant active;
  b) triethyl hexanoin,
  c) at least one additional non-volatile oil, and
  d) from 15 to 28 wt. %, based on the total weight of the composition, of wax structurant,
wherein:
  the ratio, by weight, of triethylhexanoin to additional non-volatile oil is from 2.51 to 1:1.5;
  in combination, triethylhexanoin and additional non-volatile oil provide from 40 to 60% of the total weight of the composition;
  the composition contains from 0 to 5 wt. % of volatile silicone oil; and
  the composition is in the form of an anhydrous suspension stick.

Method of Manufacture

The compositions according to the present invention can be made conveniently in accordance with processes that are typically employed to produce structured antiperspirant compositions in the form of solids or soft solids.

One suitable general method of manufacture of a solid or a soft or semi-solid stick comprises the steps of
  a) forming a mixture of an oil phase with the structurant dispersed therein;
  b) heating the mixture to an elevated temperature at which the structurant becomes molten or dissolved in the oil phase;
  c) introducing particulate astringent antiperspirant salt into the oil phase, (step (c) being carried out before, after or simultaneously with steps (a) or (b));
  d) introducing the resultant mixture into a dispenser and
  e) cooling or allowing said resultant mixture to cool to below its setting temperature, at least part of this step optionally occurring before step (d).

The temperature to which the dispersed mixture is heated in step (b) is typically in the range of from 75 to 95° C.

The order of introduction of the other ingredients is at the discretion of the manufacturer. It will be recognised that optional ingredients, if any, can be introduced at a convenient step in the process. Thus, any temperature sensitive ingredient, for example, fragrance, is desirably introduced into the composition shortly before the dispenser is charged, and preferably at a temperature within 10° C. of the setting temperature.

The compositions produced herein are suitable for dispensing from cosmetic dispensers. Such dispensers commonly comprise a barrel, often of round or oval transverse cross section, having an opening at a first end through which the composition is dispensed and an advancing mechanism at an opposed second end that can be used to move the stick composition through the dispenser. Suitable dispensers for firm sticks are described, for example in U.S. Pat. Nos. 4,232,977, 4,605,330, WO09818695, WO09603899, WO09405180, WO09325113, WO09305678, EP1040445, U.S. Pat. Nos. 5,997,202, 5,897,263, 5,496,122, 5,275,496, 6,598,767, 6,299,369, or WO 2002/03830.

The compositions of the present invention can be topically applied to skin, particularly to underarm skin, by extruding the composition in stick form above the top of the barrel and thereafter wiping the stick across the skin surface, thereby depositing a fraction of the composition on the skin. The action can be repeated until the user considers that sufficient composition has been deposited, often in the region of 3 to 8 wipes per armpit. The composition is commonly applied shortly after the armpit has been washed or shaved. The composition is thereafter left in place, conventionally, for a period of time commonly between 5 and 24 hours until it is washed off, usually using soap or a conventional shower gel, and water, for example applied using a flannel, loofah, sponge or even fingers. When seeking to inhibit perspiration, the weight of antiperspirant active applied per armpit is often in the range of from 0.05 to 0.25 grams.

Except in the operating and comparative examples, or where otherwise explicitly indicated, all numbers in this description indicating amounts or ratios of materials, conditions of reaction; physical properties of materials and/or use; dimensions and dimension ratios, are to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above. It should be noted that in specifying any range of concentration or amount, any particular upper concentration or amount can be associated with any particular lower concentration or amount.

All parts, percentages, ratios, and proportions referred to in the subject specification and in the appended claims are by weight unless otherwise indicated.

The following non-limiting examples are provided to further illustrate the invention; the invention is not limited thereto.

EXAMPLES

Cyclomethicone-containing wax stick compositions having the formulations described in Tables 1 to 3 were made using standard processing techniques. The oils, structurant, antiperspirant active, and, if present, wash-off agent were blended together and heated to approximately 90° C., by which time the wax-like materials had melted to form a homogenous mixture. If present, silica and talc were added, and the mixture was permitted to cool while maintaining stirring until its temperature had reached about 70° C., whereupon the antiperspirant active was introduced followed by the fragrance. When the mixture reached about 60° C., it was poured into conventional stick dispensers equipped with a platform and twist-up mechanism.

TABLE 1

C1A BASE COMPOSITION

| INCI Name | % w/w |
|---|---|
| Cyclomethicone (D5) | 29.95 |
| Dimethicone (50 cst.) | 1.00 |
| Butylated hydroxyl toluene (BHT) | 0.05 |
| PPG-14 Butyl Ether | 9.50 |
| C12-15 Alkyl Benzoate | 15.00 |
| Stearyl Alcohol | 18.00 |
| Hydrogenated Castor Oil (MP 80° C.) | 3.50 |
| Polyethylene (MP 84-86° C.) | 1.00 |
| Steareth - 100 | 0.50 |
| Aluminum Zirconium Tetrachlorohydrex Gly | 20.00 |
| Sunflower Seed Oil | 0.50 |
| Fragrance Oil | 1.00 |
| TOTAL | 100.00 |

TABLE 2

C1B BASE COMPOSITION

| INCI Name | % w/w |
|---|---|
| Cyclomethicone (D5) | 30.95 |
| PPG-14 Butyl Ether | 17.50 |
| Butylated Hydroxyl Toluene (BHT) | 0.05 |
| Stearyl Alcohol | 17.50 |
| Castor Wax (MP 80° C.) | 2.50 |
| PEG-8 Distearate | 2.00 |
| Talc | 2.00 |
| Aluminum Zirconium Tetrachlorohydrex Gly | 25.00 |
| Fragrance Oil | 1.00 |
| Encapsulated Fragrance Oil (contains 60 wt. % starch) | 1.50 |
| TOTAL | 100.00 |

TABLE 3

C1C BASE COMPOSITION

| INCI Name | % w/w |
|---|---|
| Cyclomethicone (D5) | 28.95 |
| Dimethicone (50 cst.) | 1.50 |
| PPG-14 Butyl Ether | 14.00 |
| C12-15 Alkyl Benzoate | 12.00 |
| Butylated Hydroxyl Toluene (BHT) | 0.05 |
| Steareth 100 | 0.50 |
| Fumed Silica | 0.50 |
| Castor Wax (MP 80° C.) | 12.00 |
| Polyethylene (MP 84-86° C.) | 3.00 |
| Paraffin Wax (MP 64-65° C.) | 2.00 |
| Aluminum Zirconium Tetrachlorohydrex Gly | 24.00 |
| Sunflower Seed Oil | 0.50 |
| Fragrance Oil | 1.20 |
| TOTAL | 100.00 |

Volatile oil-free variations of the C1A-C3A composition were prepared, by replacing cyclomethicone with a like amount of the non-volatile emollients described in Table 4.

The compositions were prepared and fabricated into stick products following the procedure described above.

TABLE 4

Non-Volatile Emollient Oils

| Non-Volatile Emollient Oil | Supplier | Composition(s) in which the non-vol. emollient oil is employed |
|---|---|---|
| Tegosoft ® DEC Diethylhexylcarbonate | Evonik Industries | C2A |
| Schercemol ™ DIS Diisostearyl Malate | Lubrizol | C3A |
| Schercemol ™ DIA Diisopropyl Adipate | Lubrizol | C4A |
| Schercemol ™ CO Ester Cetyl Ethyl Hexanoate | Lubrizol | C5A |
| Prisorine 2021 Isopropyl Isostearate | Croda | C6A |
| Cetiol ® Sensoft Propyl Heptyl Caprylate | Cognis Corp. | C7A |
| Cetiol ® CC Dicaprylyl Carbonate | Cognis Corp. | C8A |
| Crodamol ™ STS PPG-3-Benzyl Ether Myristate | Croda | C9A, C9B, C9C |
| Eutanol ® G16 Hexyldecanol | Cognis Corp. | C10A |
| Cetiol ® S Diethylhexylcyclohexane | Cognis Corp. | C11A |
| Schercemol ™ NGDO Neopentyl Glycol Diethylhexanoate | Cognis Corp. | C12A |
| Schercemol ™ IDO Isodecyl Oleate | Cognis Corp. | C13A |
| Lilac Oil | | C14A |
| Crodamol ™ CAP Cetearyl Ethylhexanoate and Isopropyl Myristate | Croda | C15A |
| Crodamol ™ DA Diisopropyl Adipate | Croda | C16A |
| Sonnecone ™ Petrolatum (a semi-solid) | Sonneborn | C17A, C17B, C17C |
| Estol ™ 3609 Triethylhexanoin | Uniqema | E1A |
| Crodamol ™GTEH Triethylhexanoin | Croda | E1B, E1C |

The compositions were evaluated in a series of panel tests. The panel tests were carried out by trained and qualified descriptive panelists. The panelists were instructed to apply 6 strokes (3 up and 3 down strokes) to the underarm. In addition to rating the product as applied to the underarm, the applied product was assessed by finger (generally considered a more sensitive determination) at 5 or 10 minutes from the time of application. The panelists rated the sensory properties on a scale of 0-10. Products were blind coded and the order of the test presentation was fully randomized. Products were tested in duplicate, and the order of presentation was randomized. Products were weighed before and after use, and mean usage values were obtained. Test panel results and usage data are reported in the tables that follow.

TABLE 5

Sensory Panel 1 (11 Panelists) Table of Mean Scores*

| | C1A | C2A | C3A | C4A | E1A | C17A |
|---|---|---|---|---|---|---|
| During Application | | | | | | |
| Coolness | 1.57 | 1.79 | 1.67 | 1.85 | 1.58 | 1.64 |
| Force to Apply | 4.42 | 4.21 | 4.25 | 4.03 | 4.58 | 4.61 |
| Slipperiness (Product v. Skin) | 4.45 | 4.72 | 4.39 | 4.92 | 4.11 | 4.11 |
| Force to Spread | 4.23 | 4.27 | 4.09 | 3.98 | 4.47 | 4.37 |

TABLE 5-continued

Sensory Panel 1 (11 Panelists) Table of Mean Scores*

| | C1A | C2A | C3A | C4A | E1A | C17A |
|---|---|---|---|---|---|---|
| Slipperiness (Product v Product) | 4.65 | 5.20 | 5.14 | 5.45 | 4.87 | 4.55 |
| Immediately After Application | | | | | | |
| Dryness | 7.70 | 7.66 | 7.63 | 7.66 | 7.74 | 7.60 |
| Whiteness | 0.71 | 0.71 | 0.68 | 0.75 | 0.35 | 0.29 |
| Visual Texture | 0.45 | 0.48 | 0.41 | 0.42 | 0.19 | 0.14 |
| Stickiness | 0.48 | 0.65 | 0.61 | 0.55 | 0.69 | 0.77 |
| At 2 Minutes | | | | | | |
| Dryness | 8.03 | 8.13 | 8.06 | 8.12 | 8.18 | 8.04 |
| Stickiness | 0.49 | 0.53 | 0.48 | 0.43 | 0.56 | 0.56 |
| Slipperiness | 6.85 | 6.86 | 6.86 | 6.94 | 6.80 | 6.74 |
| At 5 Minutes | | | | | | |
| Dryness | 8.62 | 8.7 | 8.61 | 8.73 | 8.69 | 8.59 |
| Whiteness | 0.28 | 0.29 | 0.29 | 0.32 | 0.12 | 0.13 |
| Visual Texture | 0.20 | 0.17 | 0.16 | 0.23 | 0.04 | 0.03 |
| Stickiness | 0.36 | 0.43 | 0.38 | 0.33 | 0.40 | 0.54 |
| Total Residue | 1.57 | 1.81 | 1.89 | 1.52 | 1.57 | 1.74 |
| At 5 Minutes Assessed with Finger | | | | | | |
| Powdery/Chalky | 0.62 | 0.63 | 0.73 | 0.76 | 0.66 | 0.09 |
| Gritty/Grainy | 0.08 | 0.02 | 0.03 | 0.01 | 0.07 | 0.02 |
| Oily | 0.57 | 1.14 | 1.05 | 1.05 | 0.64 | 0.76 |
| Greasy | 0.82 | 0.79 | 0.69 | 0.70 | 0.83 | 0.88 |
| Waxy | 0.49 | 0.22 | 0.33 | 0.29 | 0.44 | 0.28 |
| Dry Slick | 0.11 | 0.05 | 0.06 | 0.08 | 0.07 | 0.04 |
| At Five Minutes On Black Material | | | | | | |
| Rub-Off | 1.77 | 1.85 | 1.85 | 2.25 | 1.26 | 1.5 |

TABLE 6

PANEL 1 USAGE DATA

| COMPOSITION | MEAN USAGE (g) | SIG | | |
|---|---|---|---|---|
| C4A | 0.29 | a | | |
| C3A | 0.28 | a | b | |
| C2A | 0.27 | a | b | |
| E1A | 0.24 | | b | c |
| C17A | 0.24 | | b | c |
| C1A | 0.23 | | | c |

Compared to C1A, the C2A, C3A and C4A compositions were generally slipperier (product v. skin and/or product v. product) on application. Additionally, the panel test indicated that the C2A, C3A and C4A compositions were oilier than C1A when assessed with the finger at 5 minutes. C4A, C3A and C2A were also found to be softer sticks than C1A and left more white marks on rub-off. In this test, E1A generally provided comparable sensory properties to C1A, the volatile silicone oil-containing control, and scored better than C1A on visual texture and whiteness. Additionally, E1A showed improvements over C1A as regards rub-off. In this test C17A and E1A generally provided comparable sensory properties, with DA scoring better at 5 minutes in terms of stickiness, total residue and rub-off.

It is noted that triethylhexanoin was odorless and did not impart malodorous components to the E1A composition.

TABLE 7

Sensory Panel 2 (10 Panelists) Table of Mean Scores

|  | C1A | C5A | C6A | C7A | C8A | C9A |
|---|---|---|---|---|---|---|
| During Application | | | | | | |
| Coolness | 1.59 | 1.60 | 1.54 | 1.77 | 1.68 | 1.64 |
| Force to Apply | 4.57 | 4.19 | 4.19 | 3.86 | 4.28 | 4.56 |
| Slipperiness (Product v. Skin) | 4.12 | 4.55 | 4.62 | 4.89 | 4.48 | 3.93 |
| Force to Spread | 4.26 | 3.86 | 3.79 | 3.57 | 3.85 | 4.28 |
| Slipperiness (Product v Product) | 4.62 | 5.00 | 5.12 | 5.41 | 5.04 | 4.54 |
| Immediately after Application | | | | | | |
| Dryness | 7.84 | 7.68 | 7.65 | 7.71 | 7.73 | 7.73 |
| Whiteness | 0.71 | 0.45 | 0.59 | 0.80 | 0.78 | 0.26 |
| Visual Texture | 0.45 | 0.30 | 0.40 | 0.58 | 0.51 | 0.09 |
| Stickiness | 0.52 | 0.68 | 0.66 | 0.72 | 0.55 | 0.72 |
| At 2 Minutes | | | | | | |
| Dryness | 8.24 | 8.13 | 8.09 | 8.13 | 8.31 | 8.19 |
| Stickiness | 0.40 | 0.50 | 0.59 | 0.53 | 0.42 | 0.61 |
| Slipperiness | 6.78 | 6.74 | 6.81 | 6.79 | 6.76 | 6.71 |
| At 5 Minutes | | | | | | |
| Dryness | 8.66 | 8.57 | 8.59 | 8.45 | 8.66 | 8.56 |
| Whiteness | 0.30 | 0.16 | 0.22 | 0.41 | 0.32 | 0.11 |
| Visual Texture | 0.14 | 0.04 | 0.13 | 0.24 | 0.20 | 0.03 |
| Stickiness | 0.33 | 0.48 | 0.58 | 0.42 | 0.35 | 0.51 |
| Total Residue | 1.60 | 1.68 | 1.82 | 1.92 | 1.77 | 1.81 |
| At 5 Minutes Assessed with Finger | | | | | | |
| Powdery/Chalky | 0.67 | 0.55 | 0.65 | 0.62 | 0.60 | 0.58 |
| Gritty/Grainy | 0.0 | 0.01 | 0.0 | 0.09 | 0.05 | 0.04 |
| Oily | 0.54 | 0.89 | 1.06 | 1.28 | 0.98 | 0.68 |
| Greasy | 0.75 | 0.79 | 0.67 | 0.57 | 0.70 | 0.75 |
| Waxy | 0.46 | 0.42 | 0.34 | 0.30 | 0.36 | 0.42 |
| Dry Slick | 0.06 | 0.06 | 0.06 | 0.07 | 0.09 | 0.05 |
| At 5 Minutes on Black Material | | | | | | |
| Rub-Off | 1.93 | 1.61 | 1.85 | 2.17 | 2.02 | 1.42 |

TABLE 8

PANEL 2 USAGE DATA

| COMPOSITION | MEAN USAGE (g) | SIG | | |
|---|---|---|---|---|
| C7A | 0.32 | a | | |
| C6A | 0.29 | a | b | |
| C8A | 0.28 | | b | |
| C5A | 0.28 | | b | c |
| C9A | 0.25 | | | c | d |
| C1A | 0.23 | | | | d |

Compared to C1A, the C5A, C6A, C7A, and C8A compositions were all softer sticks that underperformed on one or more of the slipperiness and/or oiliness attributes C9A scored better than C1A on whiteness and rub-off. Otherwise, in general, C9A performed similarly to C1A in this series of tests.

The PPG-3-benzyl ether myristate was, however, extremely malodorous and negatively impacted the fragrance of the C9A composition.

TABLE 9

Sensory Panel 3 (10 Panelists) Table of Mean Scores

|  | C1A | C10A | C11A | C12A | E1A |
|---|---|---|---|---|---|
| During Application | | | | | |
| Coolness | 1.31 | 1.65 | 1.26 | 1.40 | 1.36 |
| Force to Apply | 4.70 | 3.60 | 4.36 | 4.44 | 4.83 |
| Slipperiness (Product v. Skin) | 4.06 | 5.28 | 4.43 | 4.52 | 4.02 |
| Force to Spread | 4.32 | 3.28 | 4.08 | 4.05 | 4.39 |
| Slipperiness (Product v Product) | 4.55 | 5.94 | 4.91 | 4.99 | 4.56 |
| Immediately After Application | | | | | |
| Dryness | 7.79 | 7.51 | 7.72 | 7.69 | 7.73 |
| Whiteness | 0.96 | 0.96 | 0.74 | 0.86 | 0.20 |
| Visual Texture | 0.74 | 0.85 | 0.56 | 0.60 | 0.14 |
| Stickiness | 0.61 | 0.78 | 0.58 | 0.64 | 0.59 |
| At 2 Minutes | | | | | |
| Dryness | 8.25 | 8.09 | 8.19 | 8.07 | 8.03 |
| Stickiness | 0.47 | 0.63 | 0.44 | 0.49 | 0.54 |
| Slipperiness | 6.81 | 6.69 | 6.81 | 6.82 | 6.69 |
| At 5 Minutes | | | | | |
| Dryness | 8.62 | 8.45 | 8.65 | 8.54 | 8.50 |
| Whiteness | 0.49 | 0.30 | 0.33 | 0.31 | 0.06 |
| Visual Texture | 0.39 | 0.27 | 0.23 | 0.20 | 0.04 |
| Stickiness | 0.30 | 0.60 | 0.42 | 0.39 | 0.43 |
| Total Residue | 1.40 | 1.97 | 1.70 | 1.48 | 1.48 |
| At 5 Minutes Assessed With Finger | | | | | |
| Powdery/Chalky | 0.63 | 0.64 | 0.62 | 0.69 | 0.57 |
| Gritty/Grainy | 0.02 | 0.06 | 0.03 | 0.03 | 0.02 |
| Oily | 0.58 | 2.04 | 1.12 | 0.87 | 0.69 |
| Greasy | 0.82 | 0.35 | 0.56 | 0.72 | 0.70 |
| Waxy | 0.48 | 0.21 | 0.40 | 0.36 | 0.50 |
| Dry Slick | 0.13 | 0.19 | 0.10 | 0.11 | 0.09 |
| At 5 Minutes on Black Material | | | | | |
| Rub-Off | 2.11 | 1.93 | 1.86 | 1.86 | 1.47 |

TABLE 10

PANEL 3 USAGE DATA

| COMPOSITION | MEAN USAGE (g) | SIG | | | |
|---|---|---|---|---|---|
| C10A | 0.43 | a | | | |
| C11A | 0.28 | | b | | |
| C12A | 0.26 | | b | | |
| C1A | 0.23 | | | c | d |
| E1A | 0.21 | | | | d |

The C10A, C11A and C12A compositions were softer, oilier sticks than C1A. Additionally C10A, C11A and C12A were all found to be more slippery than C1A during application on one or more attributes. C10A and C11A both had higher total residue values on the underarm at 5 minutes. E1A again showed benefits in terms of reduced white marks and rub-off, and scored better on visual texture than C1A. The results for E1A were generally similar to those obtained in Panel 1.

TABLE 11

Sensory Panel 4 (10 Panelists) Table of Mean Scores

|  | C1A | C13A | C14A | C15A | C16A | C9A |
|---|---|---|---|---|---|---|
| During Application | | | | | | |
| Coolness | 1.31 | 1.55 | 1.62 | 1.37 | 1.50 | 1.49 |
| Force to Apply | 4.70 | 4.77 | 4.34 | 4.68 | 4.51 | 5.02 |

TABLE 11-continued

Sensory Panel 4 (10 Panelists) Table of Mean Scores

| | C1A | C13A | C14A | C15A | C16A | C9A |
|---|---|---|---|---|---|---|
| Slipperiness (Product v. Skin) | 4.10 | 4.00 | 4.54 | 4.14 | 4.24 | 3.75 |
| Force to Spread | 4.32 | 4.30 | 4.04 | 4.36 | 4.12 | 4.61 |
| Slipperiness (Product v Product) | 4.71 | 4.62 | 5.15 | 4.69 | 4.82 | 4.25 |
| Immediately after Application | | | | | | |
| Dryness | 7.78 | 7.61 | 7.63 | 7.64 | 7.67 | 7.80 |
| Whiteness | 0.73 | 0.40 | 0.66 | 0.71 | 1.03 | 0.14 |
| Visual Texture | 0.53 | 0.27 | 0.51 | 0.55 | 0.81 | 0.07 |
| Stickiness | 0.64 | 0.69 | 0.58 | 0.75 | 0.58 | 0.69 |
| At 2 Minutes | | | | | | |
| Dryness | 8.12 | 8.07 | 8.18 | 8.08 | 8.09 | 8.19 |
| Stickiness | 0.51 | 0.55 | 0.47 | 0.65 | 0.35 | 0.56 |
| Slipperiness | 6.87 | 7.83 | 6.74 | 6.76 | 6.81 | 6.73 |
| At 5 Minutes | | | | | | |
| Dryness | 8.58 | 8.45 | 8.51 | 8.51 | 8.53 | 8.64 |
| Whiteness | 0.34 | 0.18 | 0.23 | 0.24 | 0.60 | 0.09 |
| Visual Texture | 0.22 | 0.11 | 0.17 | 0.17 | 0.48 | 0.03 |
| Stickiness | 0.36 | 0.40 | 0.44 | 0.52 | 0.32 | 0.51 |
| Total Residue | 1.37 | 1.53 | 1.53 | 1.63 | 1.40 | 1.24 |
| At 5 Minutes Assessed with Finger | | | | | | |
| Powdery/Chalky | 0.66 | 0.63 | 0.61 | 0.55 | 0.59 | 0.56 |
| Gritty/Grainy | 0.01 | 0.01 | 0.01 | 0.04 | 0.06 | 0.02 |
| Oily | 0.64 | 1.02 | 1.17 | 0.91 | 1.19 | 0.59 |
| Greasy | 0.68 | 0.62 | 0.49 | 0.69 | 0.43 | 0.72 |
| Waxy | 0.38 | 0.33 | 0.46 | 0.48 | 0.35 | 0.38 |
| Dry Slick | 0.17 | 0.13 | 0.11 | 0.13 | 0.09 | 0.21 |
| At 5 Minutes on Black Material | | | | | | |
| Rub-Off | 1.86 | 1.74 | 2.28 | 1.95 | 2.21 | 1.39 |

TABLE 12

PANEL 4 USAGE DATA

| COMPOSITION | MEAN USAGE (g) | SIG |
|---|---|---|
| C14A | 0.32 | a |
| C15A | 0.30 | a |
| C16A | 0.30 | a |
| C13A | 0.28 | a |
| C1A | 0.25 | b |
| C9A | 0.24 | b |

C14A, C15A, C16A and C13A were all softer sticks than C1A. Compared to C1A, C14 and C16A were significantly oilier; C14A was more slippery when applied to the skin, and both C14A and C16A were oilier when assessed with the finger at 5 minutes and had higher rub-off values. Compared to C1A, C9A scored better on whiteness immediately after application as well as at 5 minutes, and was found to have better visual texture after 5 minutes. As in the Panel 2 evaluation, C9A had a lower rub-off valued compared to C1A. C13A and C15A were shown to be generally comparable to C1A on many sensory properties (the finger assessment data at 5 minutes for C13A and C15A washigher for oiliness than C1A) and the total residue at 5 minutes was higher for C15A than C1A.

As was the case with PPG-3-benzyl ether myristate, both the isopropyl myristate and isodecyl oleate were extremely malodorous, and negatively impacted the fragrance characteristics of the C13A and C15A compositions.

TABLE 13

Sensory Panel 5 (10 Panelists) Table of Mean Scores

| | C1A | C9A | E1A | C17A |
|---|---|---|---|---|
| During Application | | | | |
| Coolness | 1.60 | 1.60 | 1.62 | 1.60 |
| Force to Apply | 4.72 | 4.81 | 5.00 | 5.15 |
| Slipperiness (Product v. Skin) | 4.11 | 3.91 | 3.78 | 3.68 |
| Force to Spread | 4.32 | 4.52 | 4.57 | 4.71 |
| Crumbling | 0.33 | 0.01 | 0.05 | 0.03 |
| Slipperiness (Product v Product) | 4.62 | 4.48 | 4.37 | 4.35 |
| Residue | 1.95 | 1.81 | 1.83 | 1.99 |
| Immediately After Application | | | | |
| Dryness | 7.68 | 7.78 | 7.72 | 7.65 |
| Coolness | 0.91 | 0.83 | 0.80 | 0.90 |
| Whiteness | 0.89 | 0.31 | 0.31 | 0.42 |
| Shine | 2.87 | 3.02 | 2.94 | 3.06 |
| Visual Texture | 0.66 | 0.19 | 0.19 | 0.30 |
| Stickiness | 0.58 | 0.70 | 0.69 | 0.83 |
| Slipperiness | 6.85 | 6.80 | 6.77 | 6.73 |
| Residue | 1.69 | 1.69 | 1.66 | 1.91 |
| At 2 Minutes | | | | |
| Dryness | 8.11 | 8.17 | 8.19 | 8.01 |
| Coolness | 0.44 | 0.45 | 0.38 | 0.53 |
| Stickiness | 0.45 | 0.54 | 0.60 | 0.70 |
| Slipperiness | 6.89 | 6.76 | 6.75 | 6.75 |
| Residue | 1.47 | 1.45 | 1.49 | 1.68 |
| At 4 Minutes | | | | |
| Dryness | 8.52 | 8.55 | 8.54 | 8.38 |
| Coolness | 0.19 | 0.24 | 0.16 | 0.32 |
| Stickiness | 0.42 | 0.47 | 0.50 | 0.63 |
| Slipperiness | 6.87 | 6.76 | 6.76 | 6.71 |
| Residue | 1.36 | 1.26 | 1.27 | 1.51 |
| At 6 Minutes | | | | |
| Dryness | 8.90 | 8.85 | 8.88 | 8.71 |
| Coolness | 0.06 | 0.11 | 0.07 | 0.19 |
| Stickiness | 0.26 | 0.38 | 0.42 | 0.50 |
| Slipperiness | 6.87 | 6.72 | 6.77 | 6.72 |
| Residue | 1.25 | 1.18 | 1.20 | 1.42 |
| At 10 Minutes | | | | |
| Dryness | 9.16 | 9.10 | 9.10 | 9.00 |
| Coolness | 0.02 | 0.02 | 0.04 | 0.07 |
| Whiteness | 0.33 | 0.07 | 0.10 | 0.19 |
| Visual Texture | 0.26 | 0.04 | 0.09 | 0.13 |
| Stickiness | 0.27 | 0.30 | 0.36 | 0.45 |
| Slipperiness | 6.84 | 6.76 | 6.78 | 6.72 |
| Residue | 1.21 | 1.09 | 1.14 | 1.32 |
| At 10 Minutes (Assessed with the Finger) | | | | |
| Slipperiness | 6.97 | 7.13 | 7.09 | 7.18 |
| Stickiness | 0.38 | 0.58 | 0.48 | 0.70 |
| Total Residue | 1.40 | 1.65 | 1.65 | 1.90 |
| Total Particulates | 0.70 | 0.77 | 0.69 | 0.73 |
| Powdery/Chalky | 0.62 | 0.60 | 0.54 | 0.59 |
| Gritty/Grainy | 0.00 | 0.00 | 0.00 | 0.00 |
| Filmy | 1.59 | 1.94 | 1.88 | 2.11 |
| Oily | 0.29 | 0.53 | 0.55 | 0.60 |
| Greasy | 0.68 | 0.67 | 0.81 | 0.98 |
| Waxy | 0.51 | 0.56 | 0.44 | 0.49 |
| Dry Slick | 0.13 | 0.10 | 0.08 | 0.06 |
| At 10 Minutes on Black Material | | | | |
| Rub-Off | 2.15 | 1.65 | 1.48 | 1.45 |

TABLE 14

USAGE DATA PANEL 5

| COMPOSITION | MEAN USAGE (g) | SIG | |
|---|---|---|---|
| C9A | 0.26 | a | b |
| E1A | 0.30 | a | b |
| C17A | 0.27 | a | b |
| C1A | 0.24 | | b |

An additional panel study (measuring properties out to 10 minutes after application) confirmed the reduction in whiteness, improved visual texture, and reduced rub-off provided by the E1A and C9A. However, the malodor of PPG-3-benzyl ether myristate again negatively impacted fragrance. As in the panel 1 test, E1A had lower residue values than C17A.

TABLE 15

Sensory Panel 6 (10 Panelists) Table of Mean Scores

| | C1A | C12A | C13A | C15A |
|---|---|---|---|---|
| During Application | | | | |
| Coolness | 1.47 | 1.52 | 1.49 | 1.50 |
| Force to Apply | 4.65 | 4.34 | 4.46 | 4.21 |
| Slipperiness (Product v. Skin) | 4.13 | 4.57 | 4.32 | 4.65 |
| Force to Spread | 4.14 | 3.91 | 4.10 | 3.81 |
| Crumbling | 0.17 | 0.13 | 0.09 | 0.12 |
| Slipperiness (Product v Product) | 4.75 | 5.17 | 5.01 | 5.22 |
| Residue | 1.88 | 1.89 | 1.86 | 1.90 |
| Immediately after Application | | | | |
| Dryness | 7.70 | 7.63 | 7.67 | 7.66 |
| Coolness | 0.78 | 0.85 | 0.86 | 0.76 |
| Whiteness | 0.95 | 0.83 | 0.59 | 0.90 |
| Shine | 2.93 | 3.00 | 3.00 | 3.05 |
| Visual Texture | 0.60 | 0.66 | 0.44 | 0.72 |
| Stickiness | 0.44 | 0.62 | 0.59 | 0.65 |
| Slipperiness | 6.83 | 6.82 | 6.78 | 6.85 |
| Residue | 1.78 | 1.75 | 1.73 | 1.88 |
| At 2 Minutes | | | | |
| Dryness | 8.07 | 8.12 | 8.02 | 8.06 |
| Coolness | 0.47 | 0.43 | 0.50 | 0.41 |
| Stickiness | 0.38 | 0.54 | 0.50 | 0.51 |
| Slipperiness | 6.77 | 6.77 | 6.79 | 6.78 |
| Residue | 1.57 | 1.54 | 1.60 | 1.64 |
| At 4 Minutes | | | | |
| Dryness | 8.48 | 8.47 | 8.37 | 8.42 |
| Coolness | 0.27 | 0.25 | 0.26 | 0.22 |
| Stickiness | 0.35 | 0.44 | 0.44 | 0.43 |
| Slipperiness | 6.85 | 6.82 | 6.78 | 6.80 |
| Residue | 1.36 | 1.35 | 1.39 | 1.42 |
| At 6 Minutes | | | | |
| Dryness | 8.74 | 8.77 | 8.65 | 8.69 |
| Coolness | 0.10 | 0.06 | 0.12 | 0.09 |
| Stickiness | 0.24 | 0.33 | 0.35 | 0.34 |
| Slipperiness | 6.83 | 6.82 | 6.81 | 6.81 |
| Residue | 1.29 | 1.25 | 1.25 | 1.32 |
| At 10 Minutes | | | | |
| Dryness | 9.07 | 9.11 | 8.99 | 8.98 |
| Coolness | 0.01 | 0.03 | 0.04 | 0.02 |
| Whiteness | 0.37 | 0.33 | 0.18 | 0.23 |
| Visual Texture | 0.29 | 0.26 | 0.15 | 0.15 |
| Stickiness | 0.19 | 0.25 | 0.29 | 0.30 |
| Slipperiness | 6.84 | 6.86 | 6.83 | 6.82 |
| Residue | 1.20 | 1.20 | 1.20 | 1.27 |
| At 10 Minutes (Assessed with the Finger) | | | | |
| Slipperiness | 7.03 | 7.30 | 7.30 | 7.34 |
| Stickiness | 0.36 | 0.47 | 0.61 | 0.64 |
| Total Residue | 1.45 | 1.87 | 2.05 | 2.01 |
| Total Particulates | 0.64 | 0.66 | 0.71 | 0.80 |
| Powdery/Chalky | 0.62 | 0.56 | 0.58 | 0.63 |
| Gritty/Grainy | 0.00 | 0.00 | 0.22 | 0.00 |
| Total Filmy Residue | 1.81 | 2.09 | 2.16 | 2.30 |
| Oily | 0.50 | 0.90 | 0.90 | 1.21 |
| Greasy | 0.77 | 0.74 | 0.84 | 0.56 |
| Waxy | 0.40 | 0.32 | 0.30 | 0.30 |
| Dry Slick | 0.12 | 0.06 | 0.08 | 0.17 |
| Rub-Off | 2.09 | 1.98 | 1.90 | 2.10 |

TABLE 16

USAGE DATA PANEL 6

| COMPOSITION | MEAN USAGE (g) | SIG | |
|---|---|---|---|
| C15A | 0.31 | a | |
| C12A | 0.30 | a | |
| C13A | 0.28 | a | |
| C1A | 0.23 | | b |

An additional panel study of C12A, C13A and C15A confirmed the sticks to be softer, sticks than C1A. The C12A, C13A and C15A compositions also tested as oilier than C1A in the finger assessment at 10 minutes. To a greater or less extent, the C12A, C13A and C15 compositions tested as more slippery than C1A and/or as leaving a more filmy residue.

TABLE 17

Sensory Panel 7 (8 Panelists) Table of Mean Scores

| | C1B | E1B | C9B | C17B |
|---|---|---|---|---|
| During Application | | | | |
| Coolness | 1.3 | 1.4 | 1.5 | 1.4 |
| Force to Apply | 5.2 | 5.8 | 6.0 | 5.2 |
| Slipperiness (Product v. Skin) | 3.3 | 2.8 | 2.8 | 3.8 |
| Force to Spread | 4.8 | 5.6 | 5.6 | 4.7 |
| Crumbling | 0.2 | 0.0 | 0.0 | 0.0 |
| Slipperiness (Product v Product) | 4.0 | 3.2 | 3.2 | 4.5 |
| Residue | 2.0 | 1.8 | 1.9 | 1.9 |
| Immediately after Application | | | | |
| Dryness | 7.8 | 7.9 | 8.0 | 7.8 |
| Coolness | 0.7 | 0.7 | 0.7 | 0.7 |
| Whiteness | 0.9 | 0.5 | 0.2 | 0.4 |
| Shine | 2.9 | 3.0 | 3.0 | 3.2 |
| Visual Texture | 0.6 | 0.2 | 0.1 | 0.2 |
| Stickiness | 0.6 | 0.8 | 0.8 | 0.9 |
| Slipperiness | 6.8 | 6.5 | 6.7 | 6.5 |
| Residue | 1.8 | 1.7 | 1.8 | 1.8 |
| At 2 Minutes | | | | |
| Dryness | 8.1 | 8.2 | 8.2 | 8.1 |
| Coolness | 0.5 | 0.5 | 0.5 | 0.5 |
| Stickiness | 0.4 | 0.7 | 0.7 | 0.8 |
| Slipperiness | 6.9 | 6.4 | 6.7 | 6.5 |
| Residue | 1.7 | 1.7 | 1.6 | 1.7 |
| At 4 Minutes | | | | |
| Dryness | 8.2 | 8.3 | 8.3 | 8.3 |
| Coolness | 0.4 | 0.4 | 0.3 | 0.3 |
| Stickiness | 0.4 | 0.6 | 0.4 | 0.7 |
| Slipperiness | 6.9 | 6.5 | 6.7 | 6.6 |
| Residue | 1.5 | 1.6 | 1.5 | 1.7 |

TABLE 17-continued

Sensory Panel 7 (8 Panelists) Table of Mean Scores

|  | C1B | E1B | C9B | C17B |
|---|---|---|---|---|
| At 6 Minutes | | | | |
| Dryness | 8.5 | 8.6 | 8.6 | 8.5 |
| Coolness | 0.2 | 0.2 | 0.1 | 0.2 |
| Stickiness | 0.2 | 0.5 | 0.4 | 0.7 |
| Slipperiness | 6.9 | 6.7 | 6.8 | 6.6 |
| Residue | 1.4 | 1.5 | | 1.6 |
| At 10 Minutes | | | | |
| Dryness | 8.8 | 8.9 | 8.9 | 8.8 |
| Coolness | 0.1 | 0.1 | 0.1 | 0.1 |
| Whiteness | 0.3 | 0.1 | 0.1 | 0.1 |
| Visual Texture | 0.2 | 0.1 | 0.1 | 0.1 |
| Stickiness | 0.2 | 0.3 | 0.5 | 0.3 |
| Slipperiness | 7.0 | 6.7 | 6.8 | 6.6 |
| Residue | 1.3 | 1.3 | 1.2 | 1.5 |
| Rub-Off | 3.0 | 2.3 | 2.1 | 1.8 |
| At 10 Minutes (Assessed with the Finger) | | | | |
| Slipperiness | 7.0 | 7.1 | 7.1 | 7.3 |
| Stickiness | 0.4 | 0.7 | 0.5 | 0.8 |
| Total Residue | 1.3 | 1.7 | 1.6 | 2.1 |
| Total Particulates | 0.6 | 0.7 | 0.7 | 0.8 |
| Powdery/Chalky | 0.6 | 0.5 | 0.5 | 0.6 |
| Gritty/Grainy | 0.1 | 0.0 | 0.0 | 0.0 |
| Total Filmy Residue | 1.3 | 2.1 | 1.9 | 2.3 |
| Oily | 0.2 | 0.6 | 0.3 | 0.6 |
| Greasy | 0.5 | 0.9 | 0.9 | 1.3 |
| Waxy | 0.5 | 0.5 | 0.6 | 0.5 |
| Dry Slick | 0.2 | 0.1 | 0.1 | 0.1 |

TABLE 18

USAGE DATA PANEL 7

| COMPOSITION | MEAN USAGE (g) | SIG | |
|---|---|---|---|
| C17A | 0.34 | a | |
| C9B | 0.31 | a | b |
| E1B | 0.30 | | b |
| C1B | 0.29 | | b |

The C1B base had a higher level of active (25 wt % vs. 20 wt. %) and was softer than the C1A base. Notwithstanding the higher level of active, reduced whitening, improved visual texture, and lower rub-off was observed immediately after application when the cyclomethicone of the C1B base composition was replaced with PPG-3-benzyl ether myristate, triethylhexanoin or the Sonnecone™ Petrolatum. After 10 minutes, when assessed with the finger, the E1B C9B and C17B compositions were found to leave a more filmy residue than the C1B control, and to be somewhat more greasy and/or oily. After 10 minutes, when assessed with the finger, E1B had lower residue values than C17B. The malodor of the PPG-3-benzyl ether myristate (C9B) again negatively impacted the fragrance character of the stick into which it was incorporated.

TABLE 19

Sensory Panel 8 (9 Panelists) Table of Mean Scores

|  | C1C | E1C | C9C | C17C |
|---|---|---|---|---|
| During Application | | | | |
| Coolness | 1.0 | 0.9 | 1.1 | 0.9 |
| Force to Apply | 4.0 | 3.7 | 3.6 | 4.4 |
| Slipperiness (Product v. Skin) | 5.0 | 5.6 | 5.6 | 4.7 |
| Force to Spread | 3.8 | 3.2 | 3.3 | 4.1 |
| Crumbling | 0.2 | 0.4 | 0.1 | 0.1 |
| Slipperiness (Product v Product) | 5.4 | 6.2 | 6.1 | 5.2 |
| Residue | 2.0 | 2.6 | 2.2 | 2.0 |
| Immediately after Application | | | | |
| Dryness | 7.7 | 7.4 | 7.6 | 7.6 |
| Coolness | 0.5 | 0.5 | 0.7 | 0.5 |
| Whiteness | 0.5 | 2.7 | 0.5 | 0.3 |
| Shine | 3.0 | 3.2 | 3.4 | 3.1 |
| Visual Texture | 0.4 | 1.1 | 0.4 | 0.2 |
| Stickiness | 0.8 | 1.1 | 1.1 | 1.0 |
| Slipperiness | 6.7 | 6.9 | 6.7 | 6.7 |
| Residue | 1.8 | 2.3 | 2.1 | 2.0 |
| At 2 Minutes | | | | |
| Dryness | 8.0 | 7.8 | 7.8 | 7.9 |
| Coolness | 0.3 | 0.3 | 0.4 | 0.4 |
| Stickiness | 0.7 | 1.0 | 0.8 | 0.8 |
| Slipperiness | 6.7 | 6.8 | 6.7 | 6.7 |
| Residue | 1.7 | 2.2 | 1.9 | 1.8 |
| At 4 Minutes | | | | |
| Dryness | 8.0 | 8.0 | 7.9 | 8.1 |
| Coolness | 0.2 | 0.2 | 0.3 | 0.3 |
| Stickiness | 0.6 | 0.9 | 0.8 | 0.7 |
| Slipperiness | 6.7 | 6.7 | 6.8 | 6.7 |
| Residue | 1.6 | 2.0 | 1.8 | 1.7 |
| At 6 Minutes | | | | |
| Dryness | 8.3 | 8.2 | 8.2 | 8.3 |
| Coolness | 0.3 | 0.1 | 0.2 | 0.2 |
| Stickiness | 0.5 | 0.9 | 0.8 | 0.7 |
| Slipperiness | 6.7 | 6.8 | 6.8 | 6.7 |
| Residue | 1.5 | 1.9 | 1.8 | 1.6 |
| At 10 Minutes | | | | |
| Dryness | 8.6 | 8.5 | 8.5 | 8.7 |
| Coolness | 0.1 | 0.0 | 0.1 | 0.1 |
| Whiteness | 0.2 | 0.7 | 0.2 | 0.2 |
| Visual Texture | 0.2 | 0.7 | 0.3 | 0.2 |
| Stickiness | 0.4 | 0.8 | 0.7 | 0.6 |
| Slipperiness | 6.7 | 6.8 | 6.7 | 6.7 |
| Residue | 1.5 | 1.8 | 1.85 | 1.5 |
| At 10 Minutes (Assessed with the Finger) | | | | |
| Slipperiness | 7.1 | 7.7 | 7.6 | 7.2 |
| Stickiness | 0.7 | 1.1 | 1.1 | 0.9 |
| Total Residue | 1.6 | 2.7 | 2.4 | 1.9 |
| Total Particulates | 0.7 | 0.8 | 0.8 | 0.7 |
| Powdery/Chalky | 0.6 | 0.6 | 0.7 | 0.6 |
| Gritty/Grainy | 0.2 | 0.1 | 0.1 | 0.1 |
| Total Filmy Residue | 1.7 | 3.0 | 2.3 | 2.0 |
| Oily | 0.8 | 1.4 | 1.3 | 1.1 |
| Greasy | 0.5 | 1.2 | 0.8 | 0.6 |
| Waxy | 0.3 | 0.3 | 0.2 | 0.3 |
| Dry Slick | 0.1 | 0.0 | 0.0 | 0.0 |
| Rub-Off | 1.4 | 2.6 | 1.9 | 1.0 |

TABLE 20

USAGE DATA PANEL 8

| COMPOSITION | MEAN USAGE (g) | SIG | | |
|---|---|---|---|---|
| E1C | 0.68 | a | | |
| C9C | 0.57 | | b | |
| C17C | 0.38 | | | c |
| C1C | 0.34 | | | c |

The E1C and C9C compositions were considerably softer sticks than both the C1C control and the C17 composition.

The extreme softness of the E1C and C9C compositions significantly impacted sensory properties. Additionally, fragrance of the C9C stick was negatively impacted by the malodor of the PPG-3-benzyl ether myristate component.

What is claimed is:

1. An antiperspirant composition comprising:
   a) from 10 to 35 wt. % based on the total weight of the composition, of antiperspirant active,
   b) triethylhexanoin,
   c) at least one additional non-volatile oil other than triethylhexanoin,
   d) from 15 to 28 wt. %, based on the total weight of the composition, of structurant, and
   e) optional perfume oil,
   wherein:
   the ratio, by weight, of triethylhexanoin to additional non-volatile oil (c) is from 5:1 to 1:2;
   in combination, triethylhexanoin and additional non-volatile oil (c) provide from 35 to 65% of the total weight of the composition;
   the composition contains from 0 to 5 wt. % of volatile oil other than perfume oil;
   the composition is anhydrous;
   the structurant (d) comprises linear fatty alcohol and at least one cosmetically acceptable co-structurant having a melting point from 75 to 95° C., wherein the linear fatty alcohol is present in an amount from 12 to 24 wt. %, based on the total weight of the composition, and the co-structurant is present in an amount from 2 to 8 wt. %, based on the total weight of the composition; wherein the composition is in the form of a solid stick;
   wherein the optional perfume oil (e), when present, is present in an amount from 0.001 to 5 wt. %, based on the total weight of the antiperspirant composition.

2. The antiperspirant composition according to claim 1, wherein, in combination, triethylhexanoin and additional non-volatile oil (c) provide from 40 to 60% of the total weight of the composition, and the antiperspirant active comprises astringent active salt selected from aluminum, zirconium and/or mixed aluminum/zirconium salts, optionally complexed.

3. The antiperspirant composition according to claim 1, in which volatile silicone oil is present in an amount from 0 to 3 wt. %, based on the total weight of the composition.

4. The antiperspirant composition according to claim 3 which, exclusive of perfume oil, contains from 0 to 3 wt. % of volatile oil.

5. The antiperspirant composition according to claim 1 which is free of volatile silicone oil.

6. The antiperspirant composition according to claim 1 which, exclusive of perfume oil, is free of volatile oil.

7. The antiperspirant composition according to claim 1 which contains from 25 to 35 wt. % of triethylhexanoin.

8. The antiperspirant according to claim 1 in which the co-structurant comprises castor wax.

9. The antiperspirant composition according to claim 1 in which the co-structurant comprises castor wax and polyethylene.

10. The antiperspirant composition according to claim 1 in which the ratio by weight, of triethylhexanoin to additional non-volatile oil (c) is from 2.5:1 to 1:1.5.

11. The antiperspirant composition according to claim 10 in which the ratio by weight of triethylhexanoin to additional non-volatile oil (c) is from 1.75:1 to 1:1.

12. The antiperspirant composition according to claim 1 in which the additional non-volatile oil (c) is selected from the group consisting of silicone oils, hydrocarbon oils, alcohol oils, ester oils, and ether oils, and mixtures of two or more thereof.

13. The antiperspirant composition according to claim 1 in which the additional non-volatile oil (c) comprises an aliphatic polyether and, optionally, an aromatic ester oil.

14. The antiperspirant composition according to claim 1, wherein the solid stick antiperspirant composition has a penetration value of 7-13 mm.

15. The antiperspirant composition according to claim 1 in which perfume oil is present in an amount of from 0.001 to 5 wt. %, based on the total weight of the antiperspirant composition.

* * * * *